United States Patent [19]

Dockner et al.

[11] Patent Number: 5,914,427
[45] Date of Patent: Jun. 22, 1999

[54] PREPARATION OF ω-HYDROXYESIERS OF α,β-UNSATURATED CARBOXYLIC ACIDS

[75] Inventors: Toni Dockner, Meckenheim; Gerhard Nestler, Ludwigshafen, both of Germany

[73] Assignee: BASF Aktiengesellshaft, Ludwigshafen, Germany

[21] Appl. No.: 08/990,076

[22] Filed: Dec. 12, 1997

[30] Foreign Application Priority Data

Dec. 13, 1996 [DE] Germany ............... 196 52 017

[51] Int. Cl.$^6$ .................................................. C07C 69/52
[52] U.S. Cl. ........................................................... 560/224
[58] Field of Search ............................................. 560/224

[56] References Cited

U.S. PATENT DOCUMENTS 2,692,256  10/1954  Bauer et al. .
2,877,264   3/1959  O Brien et al. .

FOREIGN PATENT DOCUMENTS 2140304   7/1995  Canada .
0 646 567  4/1995  European Pat. Off. .
0 663 386  7/1995  European Pat. Off. .
855 864  11/1952  Germany .

OTHER PUBLICATIONS

Chemical Abstracts, vol. 97, No. 5, Aug. 2, 1982, An 38466x, B.A. Trofimov, et al., "Synthesis of Vinyl Ethers and Sulfides with Methacrylate Groups".

*Primary Examiner*—Paul J. Killos
*Attorney, Agent, or Firm*—Oblon, Spivak, McClelland, Maier & Neustadt, P.C.

[57] ABSTRACT

In a process for preparing ω-hydroxyesters of α,β-unsaturated carboxylic acids, a vinyloxy ester of the carboxylic acid is treated with a strong acid in the presence of an alcohol, in particular a 1,2-diol or 1,3-diol.

24 Claims, No Drawings

PREPARATION OF ω-HYDROXYESTERS OF α,β-UNSATURATED CARBOXYLIC ACIDS

The present invention relates to a process for preparing ω-hydroxyesters of α,β- unsaturated carboxylic acids.

Hydroxy-functional esters of α,β-unsaturated carboxylic acids, in particular hydroxy-functional (meth)acrylates, are important comonomers for polymers which are used, for example, in paint dispersions, as coating resins or for preparing polyurethane resins.

DE-B-1 255 104 discloses preparing β-hydroxyalkyl esters of acrylic and methacrylic acid from the corresponding acid and 1,2-alkylene oxides (eg. ethylene oxide or propylene oxide). The process has the disadvantage that gaseous ethylene oxide or propylene oxide must be handled. In addition, longer-chain ω-hydroxyalkyl esters of α,β-unsaturated carboxylic acids cannot be prepared in a similar manner.

DE-B-1 518 572 and EP-A-465 853 describe processes for preparing ω-hydroxyesters by acid-catalyzed esterification of diols with acrylic or methacrylic acid. However, as a disadvantage in these esterification processes, cyclic ethers are formed as byproducts. As is disclosed, for example, by Bouben-Weyl, Methoden der Organischen Chemie, (Methods in organic chemistry) VI/3, 1965, p. 528, 1,4-butanediol, in the presence of strong acids, produces the cyclic ether tetrahydrofuran, which has very low biodegradability and is thus an environmental pollutant.

Since the diols have two equivalent hydroxyls, in the esterification, even in the event of a great diol excess, considerable amounts of the corresponding diesters are always formed, as is disclosed by EP-A-465 853, p. 3, lines 25–34. Fractionation of the esterification mixture by distillation is not generally possible, because of the small boiling point differences and the high boiling points, since the esters of α,β-unsaturated carboxylic acids, and in particular the esters of acrylic and methacrylic acid, are known to polymerize very readily at elevated temperatures.

Fractionating esterification mixture using column chromatography, as is disclosed, for example, by Makromol, Chem, Rapid Commun., 9 (1988), (7), pp. 503–511, and enzymatic hydrolysis of the diesters to give the corresponding monoesters of the diols, disclosed by JP-A-63 237 791, are not industrially and economically expedient, because of the low space-time yields and the high solvent requirement.

Diol, monoester and diester can be separated, as disclosed by EP-A 465 853, by extracting diester with an organic solvent and washing the extract with water to separate off the co-extracted monoester. Since high water solubility of the monoester is a prerequirement, this process is restricted to preparing esters of (meth)acrylic acid with short-chain diols.

EP-A-465 853 also discloses preparing 4-hydroxybutyl (meth)acrylate in the presence of large amounts of 1,4-butanediol di(meth)acrylate, in order to increase the yield of monoester. It is a disadvantage in this process that the large amounts of diester also have to be completely removed again and recycled to the esterification, ie. that large amounts of diester have to be recirculated. No details are given on the diester content in the monoester.

DE-A-4 228 397 describes a process for preparing hydroxyalkyl (meth)acrylates by reacting the corresponding hydroxyalkyl halides with (meth)acrylic salts. Owing to the use of halogen compounds and salt formation, this process is not harmless from the ecological viewpoint. In addition, diester-free monoester is not formed—up to 2% of diester is formed (p. 3, line 24).

U.S. Pat. No. 2,877,264 describes a process for preparing hydroxyalkyl acrylates and methacrylates by acid hydrolysis of the corresponding vinyloxyalkyl (meth)acrylates (vinylether cleavage). However, the yield leaves something to be desired; in the case of 1,2-butanediol it is only 35–51%. Further disadvantages are the high water requirement of the process and the necessity of using an additional solvent. Both complicate the work-up and pollute the environment.

U.S. Pat. No. 2,692,256 discloses preparing vinyloxyalkyl esters of unsaturated carboxylic acids by transesterification from the corresponding vinyloxy alcohols and esters of α,β-unsaturated carboxylic acids with lower alcohols in the presence of alkaline metal alkoxides or quaternary ammonium alkoxides. Disadvantages here are the laborious work-up and the unsatisfactory yields.

It is an object of the present invention to provide an environmentally acceptable and generally applicable process for preparing ω-hydroxyesters of α,β-unsaturated carboxylic acids in high yield and purity, in which no undesirable byproducts such as cyclic ethers or diesters are produced.

We have found that this object is achieved by a process for preparing ω-hydroxyesters of α,β-unsaturated carboxylic acids, in which a) an ester of the α,β-unsaturated carboxylic acid is transesterified by a vinyloxy-containing alcohol in the presence of basic catalysts to give the corresponding vinyloxy carboxylic ester and b) the vinyloxy carboxylic ester is reacted in the presence of strong acids as catalyst to give the corresponding ω-hydroxyester, which comprises carrying out step b) in the presence of an alcohol, preferably a 1,2-diol or a 1,3-diol. The course of the reaction is illustrated by reaction scheme 1.

The 1,2-diol used here as an example is ethylene glycol.
Reaction scheme 1

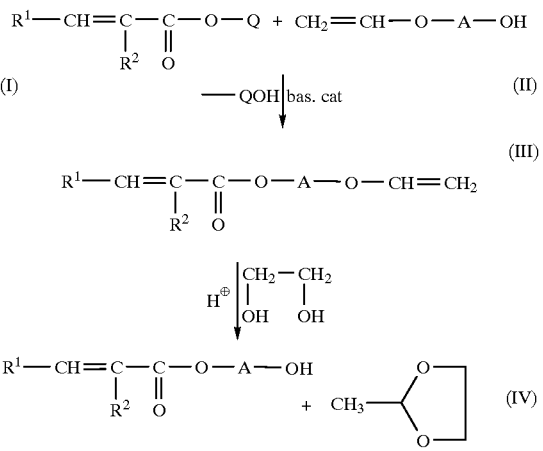

where
$R^1$ is H, or $C_1$–$C_4$-alkyl,
$R^2$ is H or $CH_3$,
A is $C_2$–$C_{12}$-alkylene, preferably $C_2$–$C_6$-alkylene,

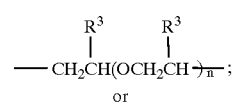

or

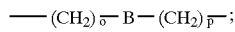

Q is $C_1$–$C_4$-alkyl, preferably $CH_3$ or $C_2H_5$,
$R^3$ is H or $CH_3$,
B is an arylene, preferably phenylene, cycloalkylene, preferably cyclopentylene or cyclohexylene, or an oxygen;
n is a number in the range from 1 to 10;
o and p independently of one another are a number in the range from 1 to 5.

The alkyls are unbranched or branched radicals such as methyl, ethyl, n-propyl, isopropyl, n-butyl, isobutyl, sec-butyl, tert-butyl, n-pentyl, isopentyl, n-hexyl and isohexyl.

$C_2$–$C_{12}$-alkylene is unbranched or branched $C_2$–$C_{12}$-alkylene, such as ethylene, n-propylene, n-butylene, 2-methylpropylene, n-pentylene, 2,2-dimethylpropylene, n-hexylene, n-heptylene, 3,3-dimethylpentylene, n-octylene, n-nonylene, n-decylene, n-undecylene and n-dodecylene.

Alcohols which can be used for the transesterification reaction in step a) are, in particular, 1,2-dimethylolcyclohexane monovinyl ether, 1,2-dimethylolbenzene monovinyl ether, 5-vinyloxypentanol, 6-vinyloxyhexanol and, particularly preferably, 4-vinyloxybutanol. Preferably, alcohol and ester components are used in a molar ration of from about 1:1.5 to 1:10, particularly preferably from about 1:2 to 1:6.

Basic transesterification catalysts are known to those skilled in the art. Suitable examples are alkaline metal alkoxides, such as potassium t-butoxide, sodium methoxide, sodium ethoxide and potassium propoxide, as well as quaternary ammonium alkoxides, such as tetramethylammonium methoxide, tetramethyl ammonium tert-butoxide, trimethylbenzylammonium ethoxide and, in particular, zirconium acetylacetonates, dialkyltin oxides, lithium salts or calcium salts, such as LiCl, $LiNO_3$, $Ca(NO_3)_2$, $CaCl_2$, or lithium oxide or hydroxide, or calcium oxide or hydroxide, or mixtures of these, and, particularly preferably, titanium alkoxides. The catalysts are expediently used in an amount of from 0.05 to 10% by weight, in particular from 0.1 to 5% by weight, in each case based on the reaction mixture.

The polymerization inhibitors used are, eg. phenothiazine, hydroquinone, hydroquinone monomethyl ether, or mixtures of these with or without air (from 0.1 to 10 l/hour×1) in an amount of from 100 to 5000 ppm, based on the reaction mixture.

The transesterification reaction temperature is generally from about 50 to 150° C., preferably from about 70 to 130° C.

The reaction time can be varied in a broad range, It is generally from about 1 to 10, preferably from about 1 to 6 hours.

The reaction can be carried out under atmospheric, superatmospheric or reduced pressure. It can be carried out continuously or batchwise.

The reaction is carried out in conventional apparatuses, eg. in a heatable stirred reactor, which may be equipped with a distillation apparatus and condenser. The reactor contents are mixed by stirring or by other conventional and appropriate measures.

The alcohol Q—OH formed in the transesterification is preferably continuously distilled off from the reaction mixture, if appropriate as an azeotrope, together with the starting ester.

The vinyloxy carboxylic ester formed by the transesterification can be obtained from the reaction mixture without prior removal of catalyst or neutralization in a conventional manner, eg. by distillation in a sieve-tray column.

In step b), in principle any alcohol can be used, but preferably 1,2-diols and 1,3-diols, but preferably those diols whose acetal boils below the reaction product. Generally, an alkanediol is used, in particular a $C_2$–$C_6$-diol. However, preference is given to 1,2-propylene glycol and particular preference is given to ethylene glycol. The 1,2-diol is generally used in an at least equimolar amount, preferably up to 30% molar excess, in particular up to 10% molar excess, based on the vinyloxy carboxylic ester.

The vinyl ether cleavage is carried out in the presence of catalytic amounts (from about 500 to 5000 ppm, based on the amount of diol used) of a strong acid. Useful strong acids are, for example, phosphoric acid, hydrogen chloride or, preferably, methanesulfonic acid or p-toluenesulfonic acid or, particularly preferably, sulfuric acid or acid ion exchangers.

The vinyl ether cleavage proceeds exothermically generally at from about 5 to 50° C., in particular at from about 20 to 40° C. It is kept within said range by cooling and/or controlling the feed rate of the vinyloxyalkyl carboxylate. The reaction time is generally from about 1 to 10 hours, in particular from about 1 to 5 hours.

The reaction is carried out in a conventional coolable and heatable reaction vessel, preferably a stirred reactor, which may be equipped with a distillation apparatus and condenser.

The reaction may be carried out continuously or batchwise. It is preferably carried out under reduced pressure (from 1 to 100 mbar).

Diol and acid are expediently charged into the reaction apparatus and the vinyloxy ester is slowly added under reaction conditions.

Alcoholysis of the vinyl ether with 1,2-diols gives the corresponding cyclic acetals, as are disclosed by, inter alia, Houben-Weyl, Methoden der Org. Chemie (Methods in organic chemistry), VI/3, 1965, pp. 329–330, which may be readily isolated by distillation. The distillation may be performed under reduced pressure or by stripping with air.

After completion of the reaction, the catalyst can be neutralized with a base, eg. alkali metal oxide or hydroxide, bicarbonate or carbonate, or alkaline earth metal oxide of hydroxide, bicarbonate or carbonate, with or without a little water, and separated off. Any excess diol still present is advantageously extracted, jointly at the same time. The end product is generally produced in adequate purity, and does not require further purification. The yield is at least 95%. An additional purification by distillation under reduced pressure may proceed in a conventional manner.

The acetal formed in the reaction is continuously distilled off.

The examples below illustrate the invention, but without restricting it to these. Percentages are mol %.

EXAMPLE 1

(Transesterification)

In a stirred reactor having an attached distillation column, a mixture of 348 g of 4-vinyloxybutanol, 1000 g of methyl methacrylate, 10.5 g of titanium tetrabutoxide, 1 g of phenothiazine and 0.5 g of hydroquinone monomethyl ether is heated to boiling, 10 l of air being continuously introduced into the reaction mixture. The methanol formed in the reaction is continuously ejected at the top of the column as an azeotrope with methyl methacrylate. After a reaction time of 5 hours, the reaction mixture is worked up by distillation under reduced pressure, the recovered excess methyl methacrylate being reused. 501 g of 4-vinyloxybutyl methacrylate (b.p. 82–83° C./4 mbar) are obtained. The yield is 91%.

EXAMPLE 2

(Vinyl Ether Cleavage)

112 g of ethylene glycol and 80 mg of sulfuric acid are introduced into a coolable stirred reactor equipped with a distillation apparatus and 333 g of 4-vinyloxybutyl methacrylate (stabilized with 350 ppm of hydroquinone monomethyl ether) are added, the pressure in the reactor being 10 mbar. The addition is controlled in such a manner that the reaction mixture does not exceed 35° C. The acetal formed in the reaction is continuously distilled off (b.p. 82° C.). After a reaction time of 3 hours, the mixture is neutralized with 0.5 g of magnesium oxide and filtered. 281 g of 4-hydroxybutyl methacrylate having a purity determined by gas chromatography of 97% (yield: 98%) are obtained. The dimethacrylate content is less than 0.1%.

We claim:

1. A process for preparing ω-hydroxyesters of α,β-unsaturated carboxylic acids, in which
   a) an ester of the α,β-unsaturated carboxylic acid is transesterified by a vinyloxy-containing alcohol in the presence of basic catalysts to give the corresponding vinyloxy carboxylic ester, and
   b) the vinyloxy carboxylic ester is reacted in the presence of strong acids as catalyst to give the corresponding ω-hydroxyester, which comprises carrying out step b) in the presence of an alcohol.

2. A process as claimed in claim 1, wherein the alcohol used is a 1,2-diol or a 1,3-diol.

3. A process as claimed in claim 1 or 2, wherein the ester of an α,β-unsaturated carboxylic acid used in step a) corresponds to the formula I

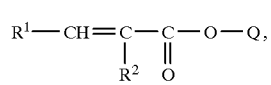 (I)

the vinyloxy-containing alcohol used in step a) corresponds to the formula II $$CH_2=CH-O-A-OH \quad (II),$$

the vinyloxy carboxylic ester prepared in step a) corresponds to the formula III

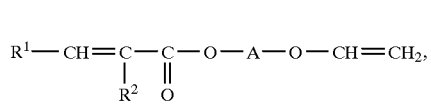 (III)

and the ω-hydroxy ester prepared in step b) corresponds to the formula IV

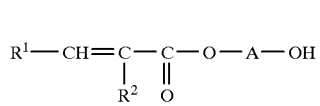 (IV)

where $R^1$ is H or $C_1$–$C_4$-alkyl, $R^2$ is H or $CH_3$,

A is a $C_2$–$C_{12}$-alkylene,

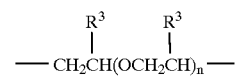

or $-(CH_2)_o-B-(CH_2)_p$,

Q is $C_1$–$C_6$-alkyl, $R^3$ is H or $CH_3$,

B is an arylene, cycloalkylene, or an oxygen, n is a number in the range from 1 to 10, and o and p independently of one another are a number in the range from 1 to 5.

4. The process as claimed in claim 1, wherein the ester of the α,β-unsaturated carboxylic acid used in step a) is an ester of acrylic or methacrylic acid with a $C_1$–$C_4$-alcohol.

5. The process as claimed in claim 1, wherein the alcohol used is 5-vinyloxypentanol, 6-vinyloxyhexanol or 4-vinyloxybutanol.

6. The process as claimed in claim 1, wherein the alcohol and ester components are used in the transesterification reaction in a molar ration of from about 1:1.5 to 1:10.

7. The process as claimed in claim 1, wherein, as basic catalysts, use is made of zirconium acetylacetonates, dialkyltin oxides, lithium salts or calcium salts or their oxides or hydroxides.

8. The process as claimed in claim 1, wherein the basic catalysts are used in an amount of from 0.05 to 10% by weight, in each case based on the reaction mixture.

9. The process as claimed in claim 1, wherein the vinyloxycarboxylic ester in step a) is purified by distillation without prior removal of the catalyst or neutralization.

10. The process as claimed in claim 1, wherein the 1,2-diol used is ethylene glycol or 1,2-propylene glycol.

11. The process as claimed in claim 1, wherein the 1,2-diol is used in from about 0 to 30%, molar excess, based on the vinyloxycarboxylic ester.

12. The process as claimed in claim 1, wherein the strong acid used is phosphoric acid, hydrogen chloride, methanesulfonic acid, p-toluenesulfonic acid, sulfuric acid or acid ion exchangers.

13. The process as claimed in claim 1, wherein step b) is carried out at reduced pressure or with air-stripping.

14. The process as claimed in claim 1, wherein step b) is carried out at reduced pressure or with air-stripping.

15. The process of claim 1, wherein B is phenylene, cyclopentylene or cyclohexylene.

16. The process of claim 1, wherein Q is $CH_3$ or $C_2H_5$.

17. The process of claim 5, wherein the alcohol is 4-vinyloxybutanol.

18. The process of claim 6, wherein the molar ratio is from about 1:2 to 1:6.

19. The process of claim 7, wherein the basic catalysts are titanium alkoxides.

20. The process of claim 8, wherein the basic catalysts are used in an amount of from 0.1 to 5% by weight, in each case based on the reaction mixture.

21. The process of claim 11, wherein the 1,2-diol is used in from about 0 to 10%, molar excess, based on the vinyloxycarboxylic ester.

22. The process of claim 12, wherein the strong acid is methanesulfonic acid or p-toluenesulfonic acid.

23. The process of claim 12, wherein the strong acid is sulfuric acid or acid ion exchangers.

24. The process of claim 13, wherein, in step b), the reaction is carried out at from about 20 to 40° C.

* * * * *

UNITED STATES PATENT AND TRADEMARK OFFICE
CERTIFICATE OF CORRECTION

PATENT NO. : 5,914,427

DATED : June 22, 1999

INVENTOR(S): Toni DOCKNER, et al.

It is certified that an error appears in the above-identified patent and that said Letters Patent is hereby corrected as shown below:

On the title page, item [54], and on top of column 1, the title should be:

--[54] PREPARATION OF ω-HYDROXYESTERS OF α, β-UNSATURATED CARBOXYLIC ACIDS--

On the title page, item [73], the assignee's name should be:

--BASF Aktiengesellschaft--

Signed and Sealed this

Thirtieth Day of May, 2000

Attest:

Q. TODD DICKINSON

Attesting Officer

Director of Patents and Trademarks